United States Patent [19]

Gualandi

[11] 4,297,233

[45] Oct. 27, 1981

[54] DEODORIZING COMPOSITION FOR ASH TRAYS

[76] Inventor: Paolo Gualandi, 16/A, Via Rosario, Bologna, Italy

[21] Appl. No.: 38,751

[22] Filed: May 14, 1979

[30] Foreign Application Priority Data

Jun. 27, 1978 [IT] Italy .................... 12684 A/78

[51] Int. Cl.$^3$ .................... C09K 3/00; A61K 7/46; C11B 9/00
[52] U.S. Cl. .................... 252/259.5; 252/522 A; 424/76
[58] Field of Search .................... 252/259.5, 88, 522 A; 424/76

[56] References Cited

U.S. PATENT DOCUMENTS

| | | | |
|---|---|---|---|
| 3,244,635 | 4/1966 | Duke | 252/88 X |
| 3,310,472 | 3/1967 | Kohl | 252/522 A X |
| 3,804,796 | 4/1974 | Alexandre | 252/522 A X |
| 3,909,461 | 9/1975 | Culmone et al. | 252/259.5 X |
| 4,020,156 | 4/1977 | Murray et al. | 252/522 A X |

FOREIGN PATENT DOCUMENTS 872181  7/1961  United Kingdom .................... 252/88

*Primary Examiner*—Richard D. Lovering

[57] ABSTRACT

A deodorizing composition, particularly for use in ash trays, in direct contact with the butts of cigarettes and cigars, comprising a granular absorbent substance which is incombustible at the combustion temperature of the glowing fire of the cigarettes or the like, containing absorbed therein an oily vapor diffuser substance. Advantageously, the absorbent substance is porous silica, having a grain size of 20 to 60 mesh per square centimeter, and an absorptive power of up to 1 part by weight of absorbed oily substance per part by weight of absorbing granular substance.

8 Claims, No Drawings

DEODORIZING COMPOSITION FOR ASH TRAYS

BACKGROUND OF THE INVENTION

1. Field of the Invention

The present invention relates to a deodorizing composition for diffusing air tempering vapors into the surrounding atmosphere. The said composition is particularly, even if not exclusively, suited for use in ash trays, and particularly in ash trays used in vehicles, e.g., automobiles, railway cars, airplanes and the like.

It is known that ash trays, particularly those of the "drawer" type or of the type provided with a closure lid, such as the ash trays used in the vehicles, have a tendency to hold combustion odors confined on their insides, releasing them suddenly into the inside of the vehicle as soon as opened, with substantial discomfort for the passengers of the vehicle, in which the said odors expand rapidly and persistently, due to the limited vehicle interior space.

The above tendency cannot be efficiently counteracted by use of known vapor diffusion devices, since the latter require a certain length of time in order to act, while the release of the combustion odor from the ash trays takes place substantially instantaneously and with a high odor concentration at the moment of opening of the ash tray.

2. Statement of the Prior Art

No relevant prior art is known to the applicant. This statement is made for the purposes of complying with the duty of disclosure under 37 CFR 1.56.

SUMMARY OF THE INVENTION

It is therefore the main object of the present invention to provide a deodorizing composition for use in ash trays, in order to obviate the above mentioned disadvantages, by effecting efficient and constant deodorization of the ash trays, concurrently with the production of the objectionable odors in the ash trays.

A further object of the present invention is a method for the manufacture of the deodorizing composition of the invention.

BRIEF DESCRIPTION OF THE PRIOR ART DEODORIZERS

Known air tempering deodorizer compositions may be subdivided into liquid type compositions which may be sprayed or evaporated into the room environment, and vapor emanating compositions embodied in solid or semi-solid carriers.

A deodorizer for use in ash trays must obviously belong to the class of the solid deodorizers. However, the known carriers utilized for the "solid" deodorizers are formed by gelatinous masses mainly of silica gel, or other organic or inorganic gelatines.

It is obvious that such a gelatinous composition cannot be used in an ash tray, in direct contact with cigarette butts or the glowing fire of cigarettes.

A base suitable for a deodorizing composition for ash trays, to be used inside the ash tray in direct contact with the cigarette butts, must meet the following requirements:

(a) It must be incombustible at the temperature of the glowing fire of the cigarettes.

(b) It must be fluid, permitting it to be poured out of the ash tray together with the cigarette butts and the ash.

(c) It must have good absorptive power for the deodorizing substances.

(d) It must be capable of gradually releasing the absorbed deodorizing substance into the surrounding environment, without being influenced by the locally high temperatures produced by the glowing fire of the cigarettes.

DESCRIPTION OF THE INVENTION

Surprisingly, it has been discovered that it is possible to obtain all the above objects, by using, as absorbent base for a deodorizing substance, a composition containing amorphous porous silica together with small amounts of metallic oxides, and preferably aluminum trioxide, calcium oxide, magnesium oxide and iron trioxide.

A preferred absorbent base composition may contain, in weight %:

$SiO_2$: from 90 to 95%, and preferably 92%
$Al_2O_3$: from 4 to 7%, and preferably 5%
$Fe_2O_3$: from 1 to 2%, and preferably 1,8%
CaO: from 0 to 0,5%, and preferably 0,2%
MgO: from 0 to 0,5%, and preferably 0,3% the remainder comprising water and/or alkalies or traces of other oxides.

The siliceous component may be porous synthetic silica, or a natural infusorial earth, as for instance Celite, Fossil Flour, Kieselguhr, Diatomite, Tripolite, Mountain Flour or the like. It is also possible to use silicates with high absorbing characteristics, such as Talc (a hydrated magnesium silicate), Bentonite (a variety of bedded clay, consisting mainly of silica, with some alumina, and smaller quantities of ferric oxide, magnesium oxide and alkalis), or like mineral silicates.

The ingredients of the above composition, in powdered form, are mixed together and transformed, by any known method, into a granular product having a grain size between 20 and 65 mesh per $cm^2$.

A typical granulometric analysis of a composition according to the invention is the following:

+20 mesh: 0.2% by weight
−20+28 mesh: 27.2% by weight
−28+65 mesh: 71.5% by weight
−65 mesh: 1.1% by weight The absorptive power of the above composition for oily essences is high, preferably between 1:1 and 1:2 parts by weight of absorbed substance per parts by weight of absorbing substance. A typical example of absorptive power between oily substance and absorbing base is represented by the ratio 44:66.

As deodorizing substances to be absorbed in the base according to the invention, any deodorizing oily essences normally employed may be used, e.g., pine essence, flowers essences, or the like.

In order to enhance the fixation of the easily evaporable oily essences, the absorbent composition with the oily essence absorbed therein is advantageously impregnated with a fixation agent, i.e., a vapor diffusion retarding substance, selected from the class comprising silicone oils, higher alcohols, or plastifiers. As an example of a suitable compound which may used as fixation agent, 1,2 propylene glycol is cited. The said fixation agent is added to the composition in amounts ranging from about 10% to about 40% of the total amount by weight of the composition, and preferably from 15 to 20 parts b.w. per 100 parts b.w. of the composition. 1,2 propylene glycol has also the additional advantage that it acts as a fungicide and antibacterial agent. A typical example of a composition according to the present invention may include (in % b.w.):
30-70% of absorbent base, as defined above
10-40% of perfumed oily essence
10-40% of fixation agent The pH of the final product is in the range of 7.
The residual humidity at 105° C. is about 0.2%

EXAMPLE

The following is a manufacturing example of a deodorizing composition according to the invention.

57 kg of granulated absorbent base material, e.g., the product sold in commerce as Celatom MP 78, are introduced into a tumbler mixer, provided with spray nozzles for spraying the deodorizing essences and the fixation agent.

25 kg of oily essence, e.g., Lavender ESM 5734 produced by Givandan, are introduced through the spray nozzles into contact with the base material inside the mixer. As soon as the perfumed oily essence has been completely absorbed by the abssorbent base material, 17 kg of 1,2 propylene glycol are added to the mixture, and mixed thoroughly therewith.

The 1,2 propylene glycol may also be partially substituted by a corresponding amount of silicone oil.

The mixture is mixed until complete absorption of the liquid components is obtained, as evidenced by the fact that the final product is a free-flowing granular substance.

It is possible to add minor amounts of coloring substances to the final product, in order to improve its appearance.

The finished product is fed to a packaging machine. Advantageously, the product is packaged into small bags each containing a dose sufficient for one ash tray.

The thus produced product is poured into the ash tray. Once exhausted, it is poured away, together with the entire contents of the ash tray.

Having thus described my invention, what I claim is:

1. A deodorizing composition comprising, in combination;
   (a) A solid absorbent granular material, of a grain size in the range of 20 to 65 mesh per $cm^2$, composed in weight % of:
   $SiO_2$: from 90 to 95%,
   $Al_2O_3$: from 4 to 7%,
   $Fe_2O_3$: from 1 to 2%,
   CaO: from 0 to 0.5%,
   MgO: from 0 to 0.5%,
   the remainder comprising water and traces of alkalies or other metallic oxides;
   (b) An oily essence absorbed in said absorbent material, the ratio of oily essence to absorbent material being, in parts by weight, in the range of 1:1.5 to 1:1; and
   (c) A vapor diffusion fixation agent selected from the class consisting of silicone oils, higher alcohols, plastifiers, and mixtures thereof.

2. A deodorizing composition according to claim 1, in which said fixation agent is contained in the composition in an amount ranging from 10% to 40% by weight of the composition.

3. A deodorizing composition according to claim 1, containing in percent by weight:
   (a) from 30 to 70% of said absorbent material;
   (b) from 10 to 40% of said oily essence; and
   (c) from 10 to 40% of said fixation agent.

4. A deodorizing composition according to claim 3, containing 57% by weight of said absorbent material.

5. A deodorizing composition according to claim 3, containing 25% by weight of said oily essence.

6. A deodorizing composition according to claim 3, containing 17% by weight of said fixation agent.

7. A deodorizing composition according to claim 3, comprising a colorant substance.

8. A deodorizing composition according to claim 1 wherein said granular material is composed of said $SiO_2$, $Al_2O_3$, $Fe_2O_3$, CaO and MgO in the following amounts by weight:
$SiO_2$: 92%
$Al_2O_3$: 5%
$Fe_2O_3$: 1.8%
CaO: 0.2%
MgO: 0.3%

* * * * *